United States Patent [19]

McGill et al.

[11] 4,405,790
[45] Sep. 20, 1983

[54] PROCESS FOR PREPARING 2-ALKYLAMINO- AND 2-AMINO-5-ALKYLPYRIDINES

[75] Inventors: Charles K. McGill; Thomas D. Bailey, both of Indianapolis, Ind.

[73] Assignee: Reilly Tar & Chemical Corp., Indianapolis, Ind.

[21] Appl. No.: 366,599

[22] Filed: Apr. 8, 1982

[51] Int. Cl.$^3$ .......................................... C07D 213/74
[52] U.S. Cl. ................................................. 546/304
[58] Field of Search ...................................... 546/304

[56] References Cited

PUBLICATIONS

Chemical Abstracts, vol. 9, pp. 1919–1920 (1915) abstracting Chichibabin and Seide "J. Russ. Phys. Chem. Soc.", vol. 49, pp. 1216–1236 (1914).
Abramovitch, "Advances in Heterocyclic Chemistry", vol. 6, pp. 274–300 (1966).

Primary Examiner—Robert T. Bond
Attorney, Agent, or Firm—Woodard, Weikart, Emhardt & Naughton

[57] ABSTRACT

An improved process for preparing the 2-alkylamino-5-alkylpyridine and 2-amino-5-alkylpyridine amination products of 3-alkylpyridines, comprising the step of initially reacting the base directly with the sodium salt of a primary alkylamine to produce the 2-alkylamino form, wherein the alkyl group in each reactant has from 1 to about 20 carbon atoms. The sodium salt is preferably preformed in situ by adding the alkylamine to a dispersion of sodium in an organic solvent heated to about 100°–120° C. The substituted amination preferably proceeds at a temperature of about 100°–140° C. in a solvent such as toluene and under an inert nitrogen atmosphere. The ratio of 2,5-:2,3- isomer products of the reaction is up to about 10:1 or more, with the effective yield of the 2,5-alkylated isomer being about 25% or more. This recovered 2-alkylamino-5-alkylpyridine product is readily dealkylated by reaction with hydrobromic or hydriodic acid with or without the presence of a pyridine hydrohalide salt to obtain the 2-amino-5-alkylpyridine product which has proven uses in herbicidal, insecticidal and pharmaceutical applications.

41 Claims, No Drawings

PROCESS FOR PREPARING 2-ALKYLAMINO- AND 2-AMINO-5-ALKYLPYRIDINES

BACKGROUND OF THE INVENTION

This invention relates generally to the field of pyridine chemistry, and in particular to direct and substituted amination reactions of 3-alkylpyridines and to an improved process for synthesizing the 2-alkylamino-5-alkylpyridine and 2-amino-5-alkylpyridine products of such reactions.

In 1914, Chichibabin and Seide first reported that α-picoline, or more commonly 2-methypyridine, underwent direct amination in the free α-position on the ring when treated with sodium amide in toluene at elevated temperatures. Chichibabin and Seide, *J. Russ. Phys. Chem. Soc.*, 46 1216 (1914). This reaction was later extended by Chichibabin and his contemporaries to amination of many pyridine, quinoline and isoquinoline bases. It has since been recognized as one of the more important and influential developments in pyridine chemistry, so much so that the reaction itself has become synonymous with the name of its principal discoverer. Its commercial importance should also not be discounted as, for example, the 2-amino amination product of pyridine itself has become an enormously important and useful starting material for further synthesis in many areas.

The first attempt known to applicants to prepare a substituted aminopyridine during amination was reported by these same authors, Chichibabin and Seide, in the same 1914 paper, as the treatment of pyridine with the sodium salt of aniline reportedly gave 2-anilinopyridine in a very small yield. Substituted Chichibabin aminations have since been extended to a limited degree as, for example, by Bergstrom et al. who reported preparing 2-methylaminopyridine, 2-butylaminopyridine, 2-cyclohexylaminopyridine, 2-n-heptylaminopyridine, 2-methylaminoquinoline, 2-butylaminoquinoline and 2-cyclohexylaminoquinoline in yields ranging from 21–73% by heating the eutectic mixture of sodamide and potassium amide with the heterocycle dissolved in the corresponding primary aliphatic amine. Bergstrom, Sturz, and Tracey, *J. Org. Chem.*, 11, 239 (1946). Abramovitch and Rogers reported that treatment of 3-picoline-1-oxide with N-phenylbenzimidoyl chloride gave predominently 2-(N-benzoylanilino)-5-methylpyridine which can be converted to 2-anilino-5-methylpyridine by hydrolysis. Abramovitch and Rogers, *J. Org. Chem.*, 39, 1802 (1974).

Most prolific in the area of substituted Chichibabin aminations have been Kovacs and Vajda, who in a series of papers reported preparing 2-butylaminopyridine, 2-butylaminoquinoline, 2-dodecylaminopyridine, 2-cyclohexylaminopyridine, 2-benzylaminopyridine, 2-dimethylaminoethylamino-6methylpyridine, 2-dimethylaminoethylaminopyridine 2-dimethylaminoethylaminoquinoline and 2-diethylaminoethylaminopyridine in yields ranging from 11–79% by replacing the amide eutectic mixture used by Bergstrom et al. with powdered sodium or potassium. In particular, their reported success in directly substituting an alkylamine at the 2-position of the pyridine ring involved heating pyridine, alpha-picoline or quinoline with the corresponding anhydrous primary alkylamine or aralkylamine in boiling toluene in the presence of powdered sodium or potassium. Kovacs and Vajda, *Acta Chim. Acad. Sci. Hung.*, 21, 445 (1959), C.A. 55, 1608b (1961); Kovacs and Vajda, *Chem. Ind.*, 259 (1959); Kovacs and Vajda, *Acta. Chim. Acad. Sci. Hung.*, 29, 245 (1961), C. A. 57, 5892h (1962); Kovacs and Vajda, *Acta Pharm. Hung.*, 31, Suppl. 72 (1961), C.A. 56, 5922e (1962).

Importantly, Kovacs and Vajda reported no reaction when only the alkylamine was heated with powdered sodium in toluene in an attempted preliminary reaction. This indicated no formation of the sodium alkylamide. They also reported low yields of the sodium salt even after long reaction times when sodamide was substituted for powdered sodium in the same reaction. They concluded that the condition for a successful substituted amination reaction required that the base and the amine react simultaneously with the powdered sodium. Vajda and Kovacs, *Rec. Trav. Chim.*, 80, 47 (1961). Moreover, under these conditions considerable amounts of dipyridyls and tarry materials are also formed because of competing reactions of sodium with the heterocyclic compound. Other efforts to prepare sodium salts of alkylamines have reported similar marginal to poor success, or in the case of one author, required a stable sodium dispersion at very low temperatures using hazardous liquid butadiene. DePree, U.S. Pat. No. 2,799,705 (1957). Without any efficient, practicable method for preparing these salts, the accepted practice at this time for substituting a heterocyclic base during a substituted Chichibabin amination remains the Kovacs and Vajda procedure of reacting the base and the amine simultaneously with powdered sodium or potassium.

Referring specifically to 3-substituted pyridines, applicants are unaware of any prior attempted substituted Chichibabin aminations of these compounds . . . successful or not. It is known that an appreciable number of these bases, and particularly the 3-alkyl derivatives, undergo simple amination with sodamide to produce predominantly a 2-amino-3-alkylpyridine reaction product ("2,3-isomer"), and to a much lesser extent a 2-amino-5-alkylpyridine ("2,5-isomer"). For example, the Chichibabin amination of 3-methylpyridine, also known as 3- or beta-picoline, with sodamide has been reported to yield these 2,3- and 2,5-isomers in a ratio of 10.5:1. Abramovitch, *Advan. Heterocycl. Chem.*, 6, 294 (1966). This is extremely unfortunate as the 2,5-isomers are much preferred because of their usefulness as starting materials and intermediates for the preparation of herbicides, insecticides and pharmaceuticals. The 2,3-isomers are comparatively of little or no use at this time, and their high yields significantly add to the expense of the process both in starting material consumed and in disposal of the 2,3-isomers. A way to improve the yield of these 2,5-isomer amination products, and of 2-amino-5-methylpyridine as being commercially most important at this time, is greatly needed.

SUMMARY OF THE INVENTION

Applicants' invention addresses this need by providing an improved process for preparing these 2,5-isomer products which involves subjecting 3-substituted bases to direct alkylamination in a substituted Chichibabin reaction. In particular, one embodiment involves the step of reacting a 3-alkylpyridine directly with a sodium alkylamide, wherein the alkyl group in each has from 1 to about 20 carbon atoms based on experiments performed to date. The reaction proceeds by reversing the previously accepted high 2,3-:2,5-isomer ratio and by selectively producing greatly improved yields of the much-preferred 2-alkylamino-5-alkylpyridine ("2,5-alkylated isomer") reaction products.

Applicants' invention also addresses the preparation of these sodium salts of primary alkylamines, and the discovery that these salts are preferably preformed prior to the alkylamination reaction. In particular, applicants have discovered a significantly improved and efficient process for preparing these salts in reasonable times by reacting the sodium source with the desired amine in the presence of a small amount of a pyridine base or quinoline base as a catalyst. Most preferred as catalysts, at least at this time, are 3- and 4-alkylpyridines and their 3,3'- and 4,4'-dialkyl-2,2'-bipyridyl dimeric equivalents, in which each alkyl group has from 1 to about 6 carbon atoms.

In a preferred form, applicants' alkylamination is accomplished by adding the selected 3-alkylpyridine base to a stirred dispersion of the sodium alkylamide which is heated to at least about 100° C. in an organic solvent such as toluene. The sodium alkylamide had been earlier preformed in the same vessel by adding the alkylamine to a heated sodium dispersion in toluene also containing a small amount of catalyst identified above. Subsequent isolation of the 2-alkylamino-5-alkylpyridine products has shown significant yields well in excess of 50% for some bases and has resulted in 2,5-:2,3-alkylated isomer ratios in excess of 10:1. These 2,5-alkylated isomers have useful biocidal properties, and are readily dealkylated in a subsequent step of applicants' invention to the more common 2-amino-5-alkylpyridine form which has known uses in the preparation of herbicides, insecticides and pharmaceuticals.

Related objects and advantages of the present invention will be apparent from the following description.

DESCRIPTION OF THE PREFERRED EMBODIMENT

For the purposes of promoting an understanding of the principles of the invention, reference will now be made to preferred embodiments of applicants' invention and specific language will be used to describe the same. It will nevertheless be understood that no limitation of the scope of the invention is thereby intended, such alterations and further modifications of the principles of the invention as described herein being contemplated as would normally occur to one skilled in the art to which the invention relates.

In its broadened form, one embodiment of applicants' invention was the discovery that significant and surprising results are achieved by subjecting various 3-substituted pyridines to direct alkylaminations with the sodium salt of various alkylamines in a substituted Chichibabin reaction. In so doing, applicants discovered that unlike aminations of such bases with sodamide, which produce high 2,3-:2,5-isomer ratios, their reaction reversed this ratio and selectively produced greatly improved yields of the much-preferred 2,5-isomer products in their alkylated amino forms. Unlike Vajda and Kovacs, applicants found that simultaneous reaction of the base with sodium and the amine is not required for successful substitution. On the contrary, applicant's work has shown it is preferred to preform the sodium salt of the alkylamine by an improved process which involves reacting the components in the presence of a catalytic agent described in detail below. In addition, applicants have discovered an improved process for dealkylating the 2-alkylamino-5-alkylpyridine products of their alkylamination reactions as also described below and in the specific examples which follow.

In its more preferred form, the alkylamination reaction was carried out in an organic solvent at a temperature appropriate for the 3-alkylpyridine used, and continued for a period of at least about 1 hour or until substantial alkylamination had occurred. No particular temperature or time period was required to achieve the successful and beneficial results of applicants' discovery. Rather, temperature and time can be and were varied depending upon the specific reactants and equipment used and upon the percent yield desired just as in standard Chichibabin aminations. From applicants' experience, a yield of about 50% or more of the 2,5-alkylated isomer product is desirable for the process to be commercially practicable, although substantially lower yields of about 25% or less can be commercially important for certain bases.

In its most preferred form, this reacting step further included the steps of preforming the sodium salt of a primary alkylamine in an inert organic solvent, bringing the resulting dispersion to a temperature of at least about 100° C., adding an amount of selected 3-alkylpyridine base to the heated dispersion, and maintaining the dispersion at or above this temperature while the base was added and for such additional time as was desired for the reaction to proceed. Toluene was the solvent of choice, and the specific temperature and time used were not critical to the benefits of reaction. For example, heating was continued for periods of about 1 to in excess of 15 hours and at temperatures of about 100° C. to over 140° C. as shown in the specific examples set forth below.

Applicants' preferred method of preforming the sodium salt of a chosen alkylamine involved reacting a sodium source with a selected primary alkylamine in the presence of a catalytic amount of a pyridine base or quinoline base. More specifically, a sodium dispersion was first prepared in a vessel by rapidly stirring an amount of sodium in an organic solvent such as toluene at a temperature of between about 100°-120° C. This preferably took place under an inert nitrogen atmosphere. With the dispersion prepared, a small amount of catalyst was added with agitation, and the temperature of the dispersion was brought to reflux at which time the selected alkylamine was added. The catalyst of choice thus far was 4-picoline. Refluxing was continued for a period of time sufficient to permit substantial formation of the sodium salt. As with the alkylamination reaction, no specific temperature or period of time was essential to the reaction. The important consideration was the formation of a substantial amount of the sodium salt for subsequent alkylamination of the pyridine base. Accordingly, reaction times were varied from about 1 or more than 12 hours, and temperatures were varied widely within the refluxing range. At the point when salt formation was sufficient, the pyridine base was added and the alkylamination step took place.

Following heating the 3-substituted base in the preformed salt dispersion to cause alkylamination to occur, the produced 2,5-alkylated isomer was isolated for subsequent use. In its most preferred form, this isolating step involved cooling and hydrolyzing the mixture after the reacting step was complete, followed by separating and fractionating the organic phase to obtain the individual 2-alkylamino-5-alkylpyridine and 2-alkylamino-3-alkylpyridine isomers. The 2,5-alkylated isomer was found to have useful biocidal properties although applicants+ most preferred embodiment included the additional step of dealkylating the recovered 2,5-alkylated isomer product.

The preferred dealkylation method involved the discovery that the 2,5- and 2,3-alkylated isomer bases dealkylated smoothly and in excellent yield when their hydrohalide salts were heated in a stream of hydrogen halide gas to release the dealkylated base and an alkyl halide and/or a corresponding olefin. Accordingly, the most preferred dealkylation procedure to date included reacting the isolated 2,5-alkylated product with hydrobromic acid or hydriodic acid to produce the dealkylated material. Applicants' testing has also shown that beneficial results are achieved when an amount of pyridine hydrohalide salt was combined with the hydrohalide salt of the 2,5-alkylated base prior to treatment with the hydrobromic or hydriodic acid. The temperature maintained during the dealkylation step ranged between about 165°–275° C. and the time involved between about 1–26 hours depending, as before, on the specific reactants used and the percent conversion desired.

Referring now to the particular reactants used thus far, and to the yields obtained, applicants' work to date has concentrated on 3-alkylpyridines and on the sodium salts of primary alkylamines, the alkyl groups in each case ranging from 1 to about 20 carbon atoms. The most preferred starting materials have been 3-picoline and sodium butylamide, which have resulted in product yields over 70% and in a 2,5-:2,3-alkylated isomer ratio in excess of 10:1 in both the 2-alkylamino and 2-amino forms. The catalyst used in preforming the sodium salt has been a pyridine base or a quinoline base compound, and more preferably a single compound or a mixture selected from the group consisting of 3- and 4-alkylpyridines, 3,3'- and 4,4'-dialkyl-2,2'-bipyridyls, 3- and 4-arylalkylpyridines and 3- and 4-alkylquinolines, in which each alkyl group has from 1 to about 6 carbon atoms and each aryl group has from 6 to about 12 carbon atoms. From experiments to date, even more preferred as the catalyst has been a single compound or a mixture selected from the group consisting of 3- and 4-alkylpyridines and their dimeric equivalents in which each alkyl group has from 1 to about 6 carbon atoms, with 4-picoline being the catalyst of choice.

For the purpose of further understanding the results of applicants' work to date and the scope and breadth of their invention as described and claimed herein, reference is now made to the specific examples and table which follow:

EXAMPLE 1

Butylamination of 3-Picoline

A sodium dispersion was prepared by stirring, under a nitrogen atmosphere, 24 g (1.04 gram atom) of sodium in 300 cc of toluene at 100°–105° C. The dispersion was made in a liter, three-neck, round bottom flask, equipped with a high speed (10,000 rpm) impeller capable of imparting high shearing action, reflux condenser, thermometer and dropping funnel. After the sodium was dispersed, 8 cc of 3-picoline was added and high speed agitation was continued about 0.5 hour until the color of the dispersion turned brown (evidence of catalyst formation). At this point, high speed agitation was replaced with slow speed paddle agitation. The dispersion was brought to reflux temperature and 73 g (1 mole) of butylamine was added dropwise in the course of 2 hours. Hydrogen was evolved indicating the formation of sodium butylamide. Refluxing was continued for 1.7 hours, when 93 g (1 mole) of 3-picoline was added over 1.5 hours (hydrogen evolution). The mixture was refluxed an additional 15 hours, after which time it was cooled and hydrolyzed with 150 cc of water. The toluene phase was separated and distilled to give 124.2 g boiling 162°–196° C. at 60 mm (freezing point 37.3° C.). A GLC analysis showed 85.6% 2-butylamino-5-methylpyridine and 8.6% 2-butylamino-3-methylpyridine (ratio of isomers 9.95:1). Yield of both isomers, 71.3%. The recovered 2-butylamino-5-methylpyridine was found to have useful biocidal properties.

EXAMPLE 2

Butylamination of 3-Picoline

A sodium dispersion of 23 g of sodium (1 gram atom) in 350 cc of toluene was prepared as described in Example 1. A catalyst was formed from 8 cc to 4-picoline. At reflux temperature, 73 g (1 mole) of butylamine was added over 2.5 hours. After an additional 3.2 hours of reflux, 93 g (1 mole) of 3-picoline was added during the course of 1.1 hours. After the picoline addition, refluxing was continued for 0.6 hours before cooling and hydrolyzing with 100 cc of water. The toluene phase was separated and distilled to give 123.5 g boiling 170° C. at 52 mm to 177° C. at 37 mm (freezing point 37.8° C.). The distillate was analyzed by GLC to show 90.3% 2-butylamino-5-methylpyridine and 5.6% 2-butylamino-3-methylpyridine (ratio of isomers 16.1:1). Yield of both isomers, 72.2%.

EXAMPLE 3

Butylamination of 3-Picoline

A sodium dispersion of 24 g sodium (1.04 gram atom) in 300 cc toluene was prepared as described in Example 1. A catalyst was formed by adding 4 cc of 4-(3-phenylpropyl) pyridine. Butylamine (73 g, 1 mole) was added at reflux temperature over 1.5 hours. After 12 hours of additional refluxing, 93 g (1 mole) of 3-picoline was added over 0.35 hours. Refluxing continued for 1.3 hours when the reaction mixture was cooled and hydrolyzed with 150 cc of water. The toluene phase was separated and distilled to give 114.2 g boiling 162°–212° C. at 85 mm (freezing point 37.5° C.). The distillate was shown by GLC to contain 87.1% 2-butylamino-5-methylpyridine and 6.8% 2-butylamino-3-methylpyridine (ratio of isomers 12.8:1). Yield of both isomers, 65.4%.

EXAMPLE 4

Butylamination of 3-Picoline

A sodium dispersion of 48 g sodium (2.09 gram atoms) in 350 cc toluene was prepared as described in Example 1. A catalyst was formed by adding 8 cc of 4-propylpyridine. Butylamine (146 g, 2 moles) was added at reflux temperature over 4 hours. After refluxing for an additional 4 hours, 186 g (2 moles) of 3-picoline was added in the course of 2 hours. Refluxing continued for 3 more hours before the reaction mixture was cooled and hydrolyzed with 200 cc of water. The toluene phase was separated and distilled to give 256.8 g boiling 155°–199° C. at 48 mm (freezing point 38.0° C.). By GLC the distillate was 85.8% 2-butylamino-5-methylpyridine and 7.0% 2-butylamino-3-methylpyridine (ratio of isomers 12.3:1). Yield of both isomers, 72.7%.

EXAMPLE 5

Butylamination of 3-Picoline

A mixture of 24 g (1 mole) of sodium hydride and 400 cc of toluene was stirred in a liter, 3 neck flask, and heated to reflux. Addition of 73 g (1 mole) of butylamine was started but the rate of formation of the sodium salt of butylamine was not practical as evidenced by the extremely slow rate of hydrogen evolution. The butylamine addition was stopped and 2 cc of 4-picoline was added. The picoline acted as a catalyst for the formation of sodium butylamide as moderate hydrogen evolution was now observed. The amine addition was resumed, taking about 1 hour. Refluxing was continued for 7.5 hours before 93 g (1 mole) of 3-picoline was added over 1.5 hours. The reaction mixture was refluxed 1 additional hour, cooled and hydrolyzed with 150 cc of water. The toluene phase was separated and distilled to give 84.1 g boiling 154°–177° C. at 23 mm. A GLC analysis showed 91.5% 2-butylamino-5-methylpyridine and 4.9% 2-butylamino-3-methylpyridine (ratio of isomers 18.7/1). Yield of both isomers, 49.4%.

EXAMPLES 6–15

Alkylamination of 3-Alkylpyridines

Procedures similar to those in Example 1 were followed for the alkylaminations of the respective 3-alkylpyridines and sodium salts of alkylamines identified in the Table which follows. Reaction times and temperatures are also given for each Example. The sodium salts had in each case been preformed in situ using the catalyst identified in the Table. The products in each Example were isolated and analyzed, and the results were as stated in the Table. The 2-alkylamino-5-alkylpyridine isomer recovered in each Example, also referred to as the 2,5-alkylated isomer for the purpose of this application, was found to have useful biocidal properties similar to the 2-butylamino-5-methylpyridine product in Examples 1–5.

EXAMPLE 16

Dealkylation of 2-Butylamino-5-methylpyridine

A 500 cc, three-neck, round bottom flask was fitted with a stirrer, thermometer, dropping funnel and a condenser for distillation. In the flask were cautiously mixed 199.9 g (1.22 mole) of 2-butylamino-5-methylpyridine prepared by the procedure of Example 1 and an equivalent amount of 48% hydrobromic acid. The solution was distilled until most of the water was removed and the liquid temperature reached 210° C. Concentrated hydrobromic acid was added dropwise at a rate of 68 g per hour to the molten 2-butylamino-5-methylpyridine hydrobromide, maintaining a liquid temperature within a range of 210°–225° C. Dealkylation took place during the hydrobromic acid addition with the formation of bromobutanes which were continuously distilled along with excess aqueous hydrogen bromide. There was also a continous evolution of noncondensable 2-butene. The two-phase condensate was separated and the aqueous acid phase was recycled until the specific gravity dropped to about 1.2. The process was stopped after 6.5 hours when there was no longer any evidence of bromobutanes in the distillate. A total of 106.2 g (0.78 mole) of bromobutanes was collected and had the composition of 83.2% 1-bromobutane and 16.8% 2-bromobutane. A material balance on hydrogen bromide showed that there was 2.04 moles consumed during the dealkylation.

When the process was finished, the molten 2-amino-5-methylpyridine hydrobromide was cooled slightly and 50 cc of water was slowly added. Cooling was continued and the solution was made basic with excess 50% caustic. The product was extracted with 150 cc of toluene and distilled to give 129.4 g of 2-amino-5-methylpyridine boiling 156–157 at 82 mm (freezing point 75.3° C.). Yield, 98.3%. The recovered 2-amino-5-methylpyridine was then used successfully as a starting material and intermediate for the preparation of herbicides, insecticides and pharmaceuticals.

TABLE

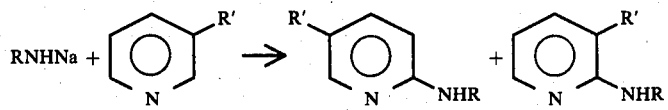

| Ex. No. | Catalyst | R | R' | T(°C.) | t(hr) | Empirical Product Formula | bp °C. | mm | % Yield Both Isomers | 2,5-:2,3- Ratio |
|---|---|---|---|---|---|---|---|---|---|---|
| 6 | 4-Picoline | Aminoethyl | Methyl | 104–110 | 2.1 | $C_8H_{13}N_3$ | 181–185 | 30 | 13.9 | 11.1:1 |
| 7 | 3-Picoline | iso-Butyl | Methyl | 102–111 | 5.9 | $C_{10}H_{16}N_2$ | 179–194 | 94 | 65.9 | 16.7:1 |
| 8 | 4-Ethylpyridine | sec-Butyl | Methyl | 100–108 | 4.6 | $C_{10}H_{16}N_2$ | 152–192 | 53 | 29.1 | 17.2:1 |
| 9 | 4-Picoline | Butyl | Butyl | 107–113 | 5.0 | $C_{13}H_{22}N_2$ | 203–221 | 59 | 85.0 | 63.9:1 |
| 10 | 4-Picoline | Cyclohexyl | Methyl | 112–114 | 1.3 | $C_{12}H_{18}N_2$ | 186–198 | 30 | 31.2 | 6.3:1 |
| 11 | 4-Picoline | Dimethylaminopropyl | Methyl | 108–112 | 3.4 | $C_{11}H_{19}N_3$ | 182–190 | 27 | 63.6 | 30.5:1 |
| 12 | 4-Picoline | Octadecyl | Methyl | 112–113 | 3.5 | $C_{24}H_{44}N_2$ | 264–281 | 9 | 39.1 | 42.7:1 |
| 13 | 3-(3-Phenylpropyl)pyridine | Butyl | 3-Phenylpropyl | 101–107 | 5.0 | $C_{18}H_{24}N_2$ | 189–199 | 0.6 | 67.1 | 49.7:1 |
| 14 | 4-Propylpyridine | Butyl | t-Butyl | 101–110 | 6.5 | $C_{13}H_{22}N_2$ | 162–170 | 0.9 | 67.7 | 65.1:1 |
| 15 | 4-Methylquinoline | Butyl | n-Nonadecyl | 131–142 | 7.0 | $C_{28}H_{52}N_2$ | 272–297 | 2 | 58.0 | 72.0:1 |

EXAMPLE 17

Dealkylation of 2-Butylamino-5-methylpyridine

This example shows that a practical rate of dealkylation was obtained at lower temperature when pyridine hydrobromide was included with 2-butylamino-5-methylpyridine hydrobromide.

In the same equipment as described in Example 16, except that a peristaltic pump was used to control the rate of hydrobromic acid addition, a mixture of 1 mole of 2-butylamino-5-methylpyridine hydrobromide and 1 mole of pyridine hydrobromide was treated with hydrobromic acid in much the same manner as described in Example 16, except that the dealkylation temperature was held at 165° C. After 26.5 hours, there was obtained 0.79 mole of 2-amino-5-methylpyridine, 0.14 mole of 2-butylamino-5-methylpyridine and 0.75 mole of bromobutanes. Yield, based on recovered 2-butylamino-5-methylpyridine, 91.9%. There was also recovered 96% of the pyridine used in the dealkylation reaction.

EXAMPLES 18-27

Dealkylation of 2-Alkylamino-5-Alkylpyridines

In each of Examples 18-27, a different one of the 2,5-alkylated isomer products from Examples 6-15 as appear in the Table was dealkylated using the same procedure described in Example 16 for temperatures between about 165°-275° C. and for periods of time ranging from about 1 to over 25 hours. The recovered 2-amino-5-alkylpyridine products were each found useful in herbicidal, insecticidal and pharmaceutical applications just as the 2-amino-5-Methylpyridine product in Examples 16 and 17.

We claim:

1. In a substituted Chichibabin amination of a 3-alkylpyridine base in an organic solvent, the improvement comprising a process for improving the ratio of 2,5-:2,3-isomer products of the reaction comprising the step of reacting the 3-alkylpyridine directly with the sodium salt of a primary alkylamine wherein each alkyl group has from 1 to about 20 carbon atoms.

2. The process in claim 1 which said reacting is at a temperature of about 100°-140° C.

3. The process in claim 2 in which said reacting is under an inert atmosphere.

4. The process in claim 3 in which said reacting is for a period sufficient to produce at least about 25% yield of the 2,5-alkylated isomer product of said reacting.

5. The process in claim 1 in which said reacting additionally comprises the steps of:
   (a) preforming the sodium alkylamide in an organic solvent dispersion at a temperature of about 100°-120° C.; and
   (b) adding the 3-alkylpyridine to the heated dispersion.

6. The process in claim 5 in which said preforming of the sodium salt of an alkylamine is further in the presence of a catalytic amount of a pyridine base or a quinoline base.

7. The process in claim 6 in which the catalyst is a single compound or a mixture selected from the group consisting of 3- and 4-alkylpyridines, 3,3'- and 4,4'-dialkyl-2,2'-bipyridyls, 3- and 4-arylalkylpyridines and 3- and 4-alkylquinolines, in which each alkyl group has from 1 to about 6 carbon atoms and each aryl group has from 6 to about 12 carbon atoms.

8. The process in claim 6 in which the catalyst is a single compound or a mixture selected from the group consisting of 3- and 4-alkylpyridines and their dimeric equivalents in which each alkyl group has from 1 to about 6 carbon atoms.

9. The process in claim 8 in which the catalyst is 4-picoline.

10. The process in claim 6 comprising the additional step of stirring the dispersion during said reacting and said adding.

11. The process in claim 10 in which the ratio of the 2,5-:2,3-alkylated isomer products of said reacting is at least about 1:1.

12. The process in claim 11 in which the yield of the 2,5-alkylated isomer product of said reacting is at least about 25%.

13. The process in claim 12 in which said reacting is of 3-picoline base directly with sodium butylamide.

14. The process in claim 13 in which said reacting is in a toluene dispersion and under an inert nitrogen atmosphere.

15. The process in claim 1 comprising the additional step of isolating the 2,5-alkylated isomer product after said reacting.

16. The process in claim 15 in which the yield of the isolated 2,5-alkylated isomer product of said reacting is at least about 25% and the ratio of the 2,5-:2,3-alkylated isomer products after said reacting is at least about 10:1.

17. The process in claim 1, 12 or 16 comprising the additional step of dealkylating the 2,5-alkylated isomer product of said reacting.

18. The process in claim 17 in which said dealkylating includes reacting the 2,5-alkylated isomer product with hydrobromic acid or hydriodic acid.

19. The process in claim 18 in which said reacting is at a temperature between about 165°-275° C. and for a period of about 1-26 hours.

20. The process in claim 19 comprising the additional step of combining an amount of pyridine hydrobromide or pyridine hydriodide salt with the 2,5-alkylated isomer product prior to said reacting with the hydrobromic or hydriodic acid.

21. The process in claim 20 in which the acid is added dropwise to the 2,5-alkylated isomer product during said reacting, and comprising the additional steps of separating and recycling the aqueous acid phase after said reacting.

22. A process for improving the 2,5-:2,3-isomer ratio of reaction products in the amination of a 3-alkylpyridine base, comprising the steps of:
   (a) providing an amount of the sodium salt of a primary alkylamine having from 1 to about 20 carbon atoms;
   (b) establishing a dispersion of the sodium alkylamide in an organic solvent;
   (c) bringing the dispersion to reflux temperature;
   (d) adding an amount of 3-alkylpyridine having from 1 to about 20 carbon atoms to the heated dispersion; and
   (e) maintaining the dispersion at reflux temperature for a period of time sufficient to allow substantial alkylamination to occur.

23. The process in claim 22 in which said bringing and said maintaining are to and at a temperature between about 100°-140° C.

24. The process in claim 23 comprising the additional step of isolating the 2,5-alkylated isomer product after said maintaining.

25. The process in claim 24 comprising the additional step of dealkylating the 2,5-alkylated isomer product after said isolating.

26. The process in claim 25 in which the ratio of the 2,5-:2,3-isomer products after said maintaining and said dealkylating is at least about 10:1.

27. The process in claim 26 in which the isolated 2,5-isomer product after said maintaining and said dealkylating is present in a yield of at least about 25%.

28. The process in claim 27 in which said providing includes preforming the sodium salt in a solvent prior to said adding.

29. The process in claim 28 in which said preforming is at a temperature between about 100°-120° C.

30. The process in claim 29 in which said preforming is further in the presence of a catalytic amount of a pyridine base or a quinoline base.

31. The process in claim 30 in which the catalyst is a single compound or a mixture selected from the group consisting of 3- and 4-alkylpyridines, 3,3'- and 4,4'-dialkyl-2,2'-bipyridyls, 3- and 4-arylalkylpyridines and 3- and 4-alkylquinolines, in which each alkyl group has from 1 to about 6 carbon atoms and each aryl group has from 6 to about 12 carbon atoms.

32. The process in claim 30 in which the catalyst is a single compound or a mixture selected from the group consisting of 3- and 4-alkylpyridines and their dimeric equivalents in which each alkyl group has from 1 to about 6 carbon atoms.

33. The process in claim 32 in which the catalyst is 4-picoline.

34. The process in claim 30 in which the alkylamine is butylamine, the solvent is toluene, and the 3-alkylpyridine is 3-picoline.

35. The process in claim 34 in which the ratio of the 2,5-:2,3-isomer products is at least about 10:1.

36. A process for preparing a sodium salt of a primary alkylamine comprising the step of reacting a sodium source directly with the alkylamine which has from 1 to about 20 carbon atoms in an organic solvent and in the presence of a catalytic amount of a pyridine base or a quinoline base.

37. The process in claim 36 in which said reacting is at a temperature between about 100°-120° C.

38. The process in claim 37 in which the catalyst is a single compound or a mixture selected from the group consisting of 3- and 4-alkylpyridines, 3,3'- and 4,4'-dialkyl-2,2'-bipyridyls, 3- and 4-arylalkylpyridines and 3- and 4-alkylquinolines, in which each alkyl group has from 1 to about 6 carbon atoms and each aryl group has from 6 to about 12 carbon atoms.

39. The process in claim 37 in which the catalyst is a single compound or a mixture selected from the group consisting of 3- and 4-alkylpyridines and their dimeric equivalents in which each alkyl group has from 1 to about 6 carbon atoms.

40. The process in claim 39 in which the catalyst is 4-picoline.

41. The process in claim 40 in which the sodium source is metallic sodium and the solvent is toluene.

* * * * *